United States Patent
Bokrantz et al.

(10) Patent No.: US 11,167,153 B2
(45) Date of Patent: Nov. 9, 2021

(54) METHOD, A USER INTERFACE, A COMPUTER PROGRAM PRODUCT AND A COMPUTER SYSTEM FOR OPTIMIZING A RADIATION THERAPY TREATMENT PLAN

(71) Applicant: RaySearch Laboratories AB, Stockholm (SE)

(72) Inventors: Rasmus Bokrantz, Stockholm (SE); Kjell Eriksson, Bålsta (SE); Tianfang Zhang, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 17/058,176

(22) PCT Filed: Jun. 10, 2019

(86) PCT No.: PCT/EP2019/065070
§ 371 (c)(1),
(2) Date: Nov. 24, 2020

(87) PCT Pub. No.: WO2019/238602
PCT Pub. Date: Dec. 19, 2019

(65) Prior Publication Data
US 2021/0213303 A1 Jul. 15, 2021

(30) Foreign Application Priority Data
Jun. 12, 2018 (EP) .................................... 18177329

(51) Int. Cl.
*A61N 5/10* (2006.01)
(52) U.S. Cl.
CPC .......... *A61N 5/1031* (2013.01); *A61N 5/1045* (2013.01)

(58) Field of Classification Search
CPC .......... A61N 5/10; A61N 5/1036; A61N 5/00; A61N 5/103; A61N 5/1038; A61N 2005/1041; A61N 2005/1039; A61N 2005/1045; A61N 5/1064; A61N 5/1071; A61N 5/1074; A61K 41/00; A61K 41/0038; G16H 50/20
See application file for complete search history.

(56) References Cited

U.S. PATENT DOCUMENTS

| | | |
|---|---|---|
| 2009/0037150 A1 | 2/2009 | Craft et al. |
| 2011/0110492 A1* | 5/2011 | Otto ........................ A61N 5/103 378/65 |

FOREIGN PATENT DOCUMENTS

EP  3 103 518 A1  12/2016

OTHER PUBLICATIONS

Hong Theodore et al., Multicriteria optimization in intensity-modulated radiation therapy treatment planning for locally advanced cancer of the pancreatic head, Int. J. Radiation Oncology Biol. Phys., vol. 72, No. 4, pp. 1208-1214, 2008.

* cited by examiner

*Primary Examiner* — Don K Wong
(74) *Attorney, Agent, or Firm* — Faegre Drinker Biddle & Reath LLP

(57) ABSTRACT

A method of obtaining an interpolated treatment plan is based on interpolating between associated dose distributions through optimization with respect to an optimization problem comprising optimization functions based on deviations from clinical goals. The method may suitably be used to improve navigated plans resulting from multi-criteria optimization.

15 Claims, 2 Drawing Sheets

METHOD, A USER INTERFACE, A COMPUTER PROGRAM PRODUCT AND A COMPUTER SYSTEM FOR OPTIMIZING A RADIATION THERAPY TREATMENT PLAN

This application is the National Stage of International Application No. PCT/EP2019/065070, filed Jun. 10, 2019, and claims benefit of European Patent Application No. 18177329.2, filed Jun. 12, 2018, the entire contents of which are incorporated by reference herein.

TECHNICAL FIELD

The present invention relates to a computer program product, a computer system and a method for optimization of radiation therapy treatment plans.

BACKGROUND

In the field of radiation therapy treatment, a key challenge is to device a high-quality plan. There is a constant search for improvement to methods of optimizing treatment plans to ensure the desired effect on a target area such as a tumor while causing as little damage as possible to healthy tissue and preferably no damage at all to organs at risk, such as the heart or the spinal cord.

One form of treatment plan optimization is multi-criteria optimization, which enables a clinician to explore different treatment options through a navigation interface. This form of optimization is based on an optimization problem comprising a set of optimization functions. Each optimization function may be an objective function or a constraint. A number of precalculated treatment plans are obtained based on the objective functions and constraints. Using the precalculated plans enables multi-criteria treatment planning in real time, by linearly navigating between the plans by adjusting the values of the objective functions.

Multi-criteria optimization of treatment plans generally starts with an optimization problem including a set of N objective functions, N being an integer greater than or equal to two. From the objective functions a set of possible treatment plans are precalculated and their resulting dose distributions are determined. Each plan is defined by a set of treatment parameters, which may be related to the fluence, or to machine parameters, for example, multileaf collimator (MLC) leaf positions, or spot weights for ion beam therapy, or seed dwell times for brachytherapy, respectively.

These possible treatment plans may be used as input data to the multi-criteria navigation process and are referred to in this document as input treatment plans, or input plans for which dose distributions are calculated. For example, approximately 50 input treatment plans and their associated dose distributions may be used. Based on the objective functions, and on the input treatment plans, a weighted combination of the dose distributions associated with the input treatment plans, is determined. This weighted combination, or weighted sum, is referred to in this document as a navigated dose distribution.

The objective functions and constraints used in multi-criteria optimization are based on quality measures for the treatment plan. An objective function is a quality measure, typically related to the dose distribution, for example, in terms of minimum or maximum dose to a specific organ. A constraint comprises a quality measure and an associated set of feasible values. The quality measures used as objectives functions and in constraints should have mathematical properties that make them suitable for optimization, such as continuity and differentiability. The quality measures used as objective functions and in constraints are typically penalties, such as quadratic penalties, on the deviation between the actual voxel dose to a structure and a reference dose level.

User interfaces have been developed that allow an operator to adjust the desired value for each objective function. One slider bar is provided for each objective function, and the operator can manipulate the slider bars. The slider movements are translated to changes of weighting of the dose distributions by a navigation algorithm that takes desired objective function values as input. To facilitate the navigation, clamps may be applied to restrict the possible range of slider movements. In the simplest embodiment, a clamp functions as an upper bound for the objective function value associated with a slider.

Mathematically, the multi-criteria optimization problem can be expressed as:

$$\text{Minimize } [f_1(x), f_2(x), \ldots f_N(x)]^T$$

Subject to x in X,
where each $f_i$ is an objective function of the multi-criteria optimization problem and x is a vector of variables. The elements of x may correspond directly machine parameters on the format that the treatment plan is transmitted to the treatment machine. The elements of x may also be a specification of the treatment plan from which the machine parameters can be derived, such as fluence distributions per beam direction. The feasible set X defines the set of variable vectors that correspond to a valid representation of a treatment plan. This set can be defined using some vector of constraint functions c, e.g. $X=\{x: c(x) \leq 0\}$. Examples of typical constraints are functions that require a minimum separation between opposing leaves within an MLC leaf pair, and lower bounds on the number of MUs per photon segment or ion spot. All objective functions $f_1, f_2, \ldots, f_N$ can be minimized without loss of generality because maximization of an objective is equivalent to minimization of the negative of the objective.

A solution x* to the multi-criteria optimization problem is said to be a Pareto optimal solution if it is feasible (x* belongs to X) and there exists no other feasible solution that has at least as good objective function value for each objective, and strictly better objective function value for at least one objective. Different Pareto optimal solutions to the multi-criteria problem can be calculated by optimizing with a scalarized counterpart of the multi-criteria problem, according to $$\text{Minimize } \Sigma_{i=1,\ldots,N} w_i f_i(x)$$

Subject to x in X,
where the nonnegative weights $w_i$ are varied to produce different solutions. Optimal solutions can be calculated by other techniques than weighted-sum scalarization, as is well-known in the field. A particular Pareto optimal solution x* defines a vector or objective function values $f(x*)$ that lies in N-dimensional space. The set of all objective function vectors associated with Pareto optimal solutions defines a surface in the N-dimensional space known in the field as the efficient frontier, the Pareto surface or the Pareto front. Since the vector of variables x defines a dose distribution, the input solutions defining the approximation of the Pareto front may be referred to as input dose distributions.

Since the vector of variables x defines a dose distribution, the input solutions defining the approximation of the Pareto front may be referred to as input dose distributions. When the Pareto front has been defined or approximated, the actual dose planning may be performed by linear interpolation of the input dose distributions, to produce a navigated dose distribution Hong et al., Multicriteria optimization in intensity-modulated radiation therapy treatment planning for locally advanced cancer of the pancreatic head, Int. J. Radiation Oncology Biol. Phys., Vol. 72, No. 4, pp. 1208-1214, 2008; discloses the use of multi-criteria optimization for treatment of pancreatic cancer. A number of plans are obtained for a patient, a Pareto surface is generated, and an operator navigates to a point on the Pareto surface that is selected to optimize the treatment. Tests showed that a navigated plan of satisfactory quality could be arrived at within a relatively short time.

When a plan has been generated, fulfilment of clinical goals determines if the treatment plan is acceptable or preferable for treatment. A clinical goal comprises a quality measure for a treatment plan and feasible set of values for the quality measure. Common types of quality measure for the clinical goals include:

- dose-volume histogram (DVH) measures that are defined for some region of interest (ROI) (a sub-region of the patient volume)
- equivalent uniform dose, which according to one definition is the a:th power mean of the dose to the ROI, where a is a preselected (usually tissue specific) parameter
- tumor control probabilities (TCPs) for targets and normal tissue complications probabilities (NTCPs) for organs at risk, which depend on some radiobiological model It can be difficult to navigate to dose distributions that precisely fulfill the clinical goals for various reasons:

- The fact that the quality measures used as objective functions and constraints generally different from the quality measures used in clinical goals means that the level of clinical goal fulfillment can only be controlled indirectly through movement of sliders that control objective function values that are correlated (but not in direct correspondence) with the clinical goal.
- A movement of a slider affecting one objective function value causes all other sliders to move to adapt. Consequently, the level of clinical goal fulfillment is therefore also generally altered.
- The slider bar positions represent linearized function values. The actual objective function value is therefore not equal to the slider function value if the function is nonlinear.

For these reasons, a considerable amount of manual fine tuning may be required before a navigated dose distribution is obtained that exactly meets the clinical goals.

Hence, there is a desire for making treatment planning involving multi-criteria optimization more efficient.

SUMMARY

It is an object of the present invention to provide a method for treatment plan optimization, in particular multi-criteria optimization, that is more efficient and user-friendly.

The invention relates to a method of optimization of a radiation treatment plan for a patient, comprising the following steps:

providing a set of input dose distributions,
defining an interpolation optimization problem based on a set of clinical goals for the patient, the interpolation optimization problem comprising a set of optimization functions, at least one optimization function representing a measure of violation of a clinical goal in the set of clinical goals,
optimizing an interpolated dose distribution based on a weighted combination of the input dose distributions, by a computer-based optimization of the interpolation optimization problem, said optimization involving determining, for each of the input dose distributions, an interpolation weight, specifying the weight to be assigned to this input dose distribution in a further optimized dose distribution, and
calculating an interpolated treatment plan based on the interpolated dose distribution.

Hence, the inventive method enables automatic calculation of an interpolated dose based directly on the deviation from one or more clinical goals. According to the invention, high-quality interpolated dose distributions fulfilling the clinical goals may be identified with little or no manual adjustment of sliders. Thus, a method is provided that is less time-consuming and also less dependent on the skills of the operator. The output of the automated navigation is an updated set of interpolation coefficients that define updated slider positions and an updated interpolated dose distribution. Basing the optimization problem directly on clinical goals means that there is a direct relationship between the desired outcome and the parameters affected in the optimization.

The method involves applying computer-based optimization for adjusting the interpolation weights of dose distributions associated with the respective input plans to match one or more clinical goals. Typically, each of the clinical goals is defined by a quality measure and a set of feasible values for the quality measure. The interpolation optimization problem may also comprise one or more constraints. In a preferred embodiment, at least one constraint corresponds to a limit restricting an objective function value of the interpolated treatment plan. Setting such a limit corresponds to setting a clamp on a slider bar.

The inventive method is not dependent on the hardware used for treatment delivery. The method is, therefore, equally valid for any treatment technique where multicriteria optimization is applicable, e.g. external beam photon therapy, electron therapy, ion beam therapy, and brachytherapy.

In some embodiments the step of providing a set of input dose distributions comprises obtaining a set of input plans and calculating and input dose distribution for each of the input plans. Alternatively, dose distributions that are not obtained from treatment plans may be used as dose distributions.

In preferred embodiments, the input dose distributions are related to treatment plans that result from multi-criteria optimization and the method enables automatic further improvement of the navigated plan resulting from the multi-criteria optimization. In this case the step of providing a set of input dose distributions comprises a. providing a multi-criteria optimization problem including a set of at least two objective functions,
b. obtaining a set of input treatment plans by optimization with respect to the multi-criteria optimization problem, and
c. calculating a set of dose distributions, each dose distribution being associated with one of the treatment plans.

Before the optimization of the interpolated dose distribution, a navigated dose distribution may be provided based on a weighted combination of the input dose distribution, in which each input dose distribution is assigned a navigation weight, and the navigation weights may be used as input values to the interpolation optimization problem.

Before the final step of converting the interpolated dose distribution to an interpolated plan, further manual navigation of the interpolated dose distribution may be performed, to obtain an interpolated plan that is even further improved.

In the simplest embodiment, the optimization towards clinical goal fulfilment is automatically started when the input plans have been generated. In another embodiment, the operator is enabled to input a start instruction, for example, press a button to start the optimization with respect to all clinical goals in one operation.

In a preferred embodiment, the operator may partition the clinical goals into priority groups. In this embodiment, the method performs a first optimization with respect to a first subset of clinical goals having a high priority followed by a subsequent optimization with respect to a second subset having a lower priority than the first subset. Several subsets of clinical goals at different priority levels may be defined for a sequence of optimization procedures for subsets of decreasing priority. For each new optimization procedure in this case, constraints may be set on the dose distribution to prevent a deterioration of the fulfilment of clinical goals having a higher priority. The constraints may be defined to allow a small deterioration compared to the level of clinical goal fulfilment obtained during the previous optimization(s), so that fulfilment of clinical goals with low priority is not completely hindered by clinical goals having higher priority.

The invention also relates to a user interface for controlling optimization of a radiation treatment plan carried out in a computer, based on a number of input treatment plans, according to any one of the preceding claims, comprising display means for displaying a list of clinical goals and an associated value range for each clinical goal, and preferably a user input means enabling a user to start optimization according to the method discussed above. For each clinical goal there is also preferably an indicator of whether the clinical goal is fulfilled. In a preferred embodiment, the list of clinical goals is also arranged to hold an associated constraint for at least one of the clinical goals, and an indicator of whether the constraint is fulfilled. Preferably, the user input means is also arranged to enable a user to enter clinical goals and/or other input data affecting the optimization problem into the computer.

The invention also relates to a computer program product for controlling a radiation therapy planning apparatus, preferably stored on a carrier such as a non-transitory storage means, said computer program product comprising computer readable code means which when run in a processor of a radiation therapy planning apparatus will cause the apparatus to perform the method according to the above. The code is preferably also arranged to cause a user interface as described above to be displayed on a screen associated with the radiation therapy planning apparatus, register an adjustment to an interpolation weight to be assigned to a treatment plan and calculate the further optimized treatment plan as a weighted sum of the input treatment plans, using each interpolation weight as a weight for its associated input treatment plan.

The invention also relates to a radiation therapy treatment planning apparatus comprising a processor and a program memory holding a computer program product according to the above arranged to be run in the processor to control the radiation therapy treatment planning apparatus to perform the inventive method.

BRIEF DESCRIPTION OF THE DRAWINGS

The invention will be described in more detail in the following, by way of example and with reference to the appended drawings, in which.

DETAILED DESCRIPTION

According to embodiments of the invention, the initial navigated dose distribution is further optimized by an automatic optimization process that will be described in the following. The process involves further interpolation between the input dose distributions and the result is referred to as an interpolated dose distribution. As will be explained, the automatic optimization process may also be performed directly on the input dose distributions without a navigated dose distribution being obtained first. The interpolated dose distribution may be converted into an interpolated plan.

Figures 1A, 1B:
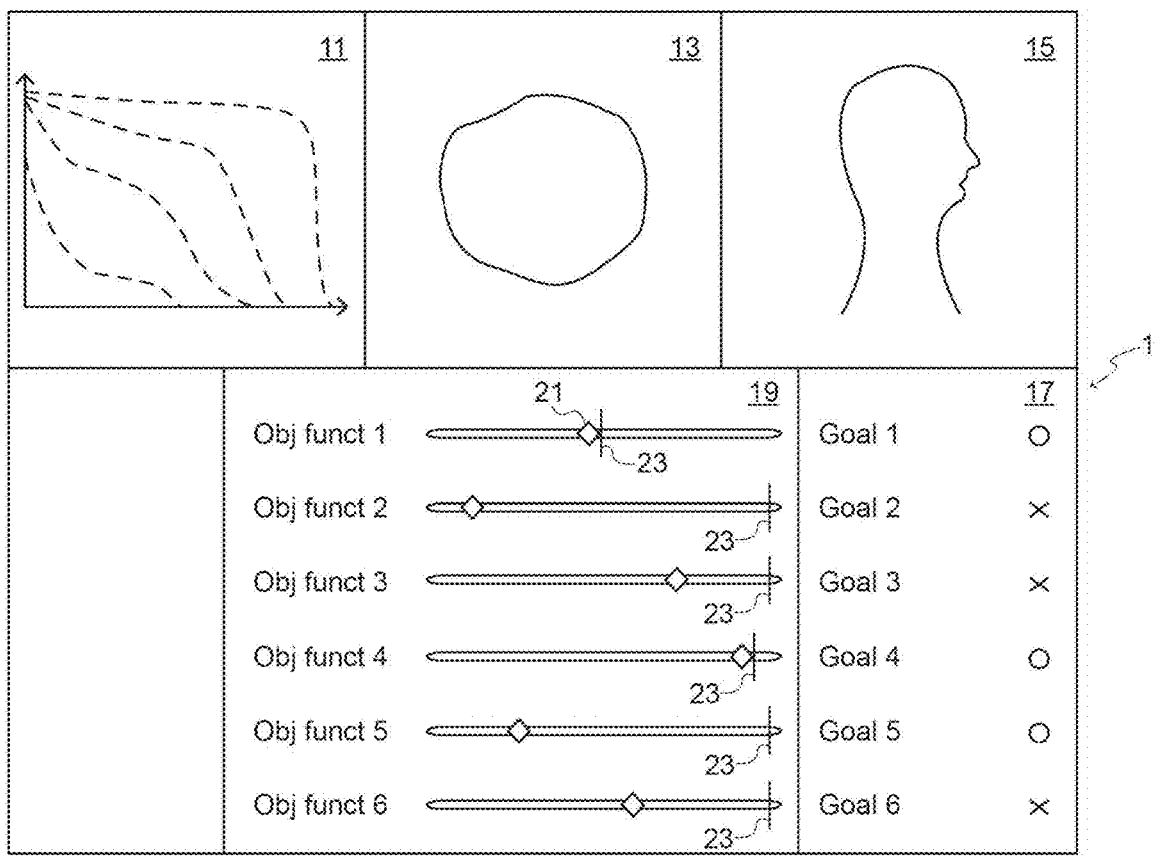
FIG. 1a illustrates a user interface for a conventional multi-criteria planning system.
FIG. 1b illustrates part of a user interface adapted to the inventive method.

FIG. 1a shows a simplified prior art treatment planning interface 1 for manual multi-criteria optimization of a treatment plan to obtain a navigated dose distribution as defined above. In the uppermost part of the interface there are three fields 11, 13, 15: a first field 11 for displaying DVH curves corresponding to a current plan, and a second 13 and a third field 15 for displaying the resulting dose distribution superimposed on the patient images seen from different angles. In this example, the second field 13 shows a section through the patient's neck and the third field 15 shows the patient's neck and head as seen from the side. For simplicity, no superimposed dose distribution is shown in this example figure.

The lowermost part of the interface has a field 17 listing clinical goals, shown to the right in FIG. 1a. The list may also comprise information about the priority assigned to each of the clinical goals, although this is not shown. The list may also show information for each clinical goal about whether or not it is met, in any suitable way. In this example, this is indicated by a 0 indicating that the goal is met or an X indicating that the goal is not met. In a practical implementation color coded dots will normally be used, typically green for goals that are met and red for goals that are not met. Of course, a range of colors indicating the magnitude of the deviation from the goals may be used and/or the actual values may be displayed as numbers. The clinical goals are typically specifications of lower bounds on the dose to targets that are to be treated and/or upper bounds on the doses to surrounding tissue and in particular to organs at risk, such as the heart or the spinal cord. It is often allowed to violate the lower or upper bound on the dose to a limited extent. Consequently, the clinical goals may be specified as upper or lower bounds on DVH measures for the structure.

In the central lower part 19 of the interface 1, there is a list of the N objective functions discussed above, and for each objective function an adjustment means in the form of a slider bar 21 which enables an operator to select the value of the respective objective function. As is common in the art, the objective functions relate to limiting the objective function value for the other objective functions when the slider bar for one objective function is moved, while fulfilling the constraints.

The operator can adjust the function value for one of the objectives of the navigated dose by manipulating the slider. All the objective functions affect each other, so that when one slider is moved, the other sliders will adjust to the new value. For example, an increased dose to one organ will affect the dose to its surrounding tissue. Also, the DVH curves in field 11 and the dose distributions in fields 13 and 15 resulting from the specified combination of the objective functions defined by the slider positions will be recalculated and displayed in real time. In this example, the leftmost slider bar positions are considered to be the most desired values, which means that the value of the objective function increases towards the right. It is possible to restrict the movement of a particular slider by defining clamps for the slider, so that undesired objective function values are prohibited. The clamps 23 are shown in FIG. 1*a* as horizontal lines where the clamps on objective functions 1 and 4 in this example actually limit the movement of the corresponding clamps, while the clamps on the other objective functions are placed in the maximum position. Placement of a clamp on a particular slider leads to a restriction of the range of feasible movements for the other sliders as well, although this is not shown in FIG. 1*a*.

The slider bars provide a particularly suitable way of adjusting the values. However, as the skilled person would understand, other ways of inputting values may also be used, for example, manually entering numbers or manipulating the size of an object on the screen. As will be understood, the clamps may be implemented as any suitable type of function restricting the function values The objective function values are used as indicators for the quality of a particular plan. There is no guarantee that currently fulfilled clinical goals remain fulfilled throughout the navigation because there is generally no one-to-one correspondence between clinical goals and objectives.

FIG. 1*b* shows a possible user interface for the inventive method, which may be displayed in an overall user interface including the three fields 11, 13, 15 in the uppermost part of FIG. 1*a*.

The user interface in FIG. 1*b* comprises a first button 30 which may be activated by a user to start multi-criteria optimization towards fulfilling the specified clinical goals, and a second button 31, which may be activated to stop an ongoing optimization. The user interface also preferably comprises a third button 32 for adjusting optimization settings, such as a number of iterations for the optimization, and/or numerical tolerances.

The user interface also has a first column 33 comprising a list of clinical goals, each related to a region of interest or a point of interest and a second column 34 comprising the value currently achieved for each clinical goal. The clinical goals are defined in manners known in the art, for example, as a minimum or maximum average dose to a region, or to a specified fraction of a region, or a minimum homogeneity index. A third column 35 displays the type of dose and a fourth column 36 displays the regions to which the clinical goals apply, typically either tumors or organs at risk. In the example, there is a first clinical goal for the planning target volume (PTV) and a second clinical goal for a clinical target volume (CTV) and a clinical goal for each of a first and second organ at risk, OAR1 and OAR2, respectively. A fifth and a sixth column 37, 38 may be used for setting a priority and/or a weight, for each of the clinical goals. A seventh column 39 may be provided to display whether or not the clinical goal is fulfilled, shown in FIG. 1*b* as an o for yes or an x for no. An eighth column 40 may be used to set a constraint for one or more of the clinical goals as desired. Of course, which columns to display may be selected as is seen fit, and information not shown in FIG. 1*b* may also be displayed.

The fourth and the fifth column are used to adjust the relative contribution of each clinical goal on the result. This may be done by including a prioritization of the clinical goals based on their importance, either by setting a priority level defining the order in which the clinical goals may be optimized in lexicographic fashion, or by assigning a weight to each clinical goal and defining an objective function in the optimization problem to minimize the weighted sum of deviations from the clinical goals.

The interface is preferably arranged to enable the user to input clinical goals, values and constraints, and to change the priority level or weight of each clinical goal. Preferably, the result of the optimization is continuously displayed in the other fields 11, 13, 15 of the interface, not shown in FIG. 1*b* and also in the table of FIG. 1*b*. It should be understood that the inventive method may be performed fully automatically, without any user interface. In this case, the system may be arranged to start interpolation automatically as soon as the input dose distributions are provided, instead of waiting for an instruction from the user clicking the "start optimization" button.

Figure 2:
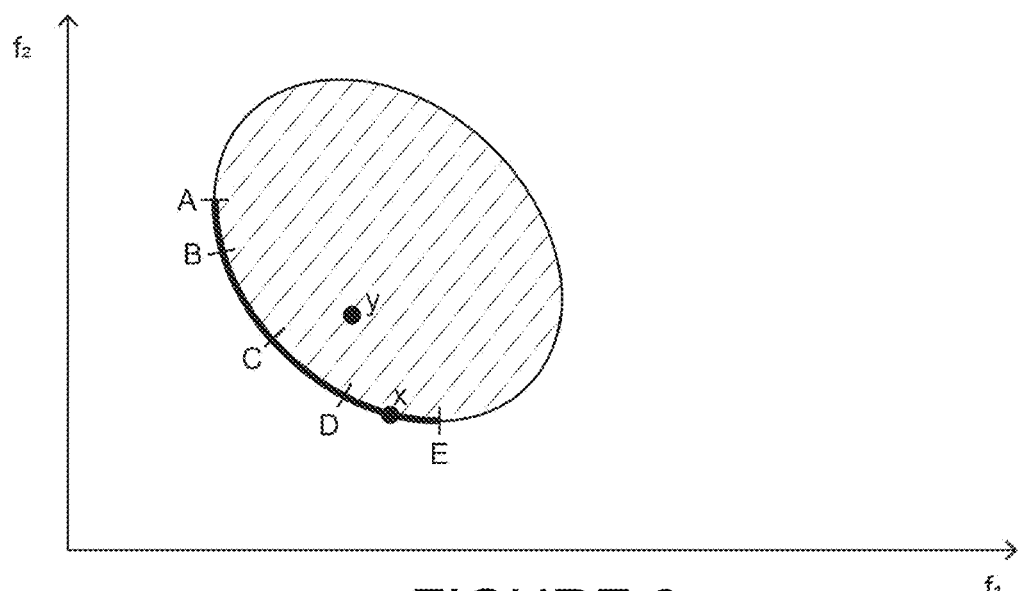
FIG. 2 illustrates a Pareto based planning system for optimizing two objective functions.

FIG. 2 illustrates the principle of multi-criteria optimization for a simplified set of objective functions. In multi-criteria optimization, a multi-criteria optimization problem is defined in terms of a set of objective functions and a set of constraints.

This is illustrated in FIG. 2 using only two objective functions $f_1$ and $f_2$ (both to be minimized), respectively, to enable a two-dimensional display. In a practical case the number of objective functions may typically be between around 10, which would require a multi-dimensional space. The region enclosed by the ellipse represent objective function vectors that correspond to feasible treatment solutions.

The curve in thick solid indicates the vectors of objective function values corresponding to Pareto optimal solutions defining achievable combinations of the two objective functions $f_1$ and $f_2$. The curve is known in multi-criteria optimization as the Pareto front. The Pareto front will be an N-dimensional surface, where N is the number of objective functions. As can be seen, in any point on the Pareto front an improvement of one of the objective functions will lead to a deterioration of the other one. Any chosen combination of the objective functions will be a trade-off based on the desired result.

The system comprises a number of input dose distributions, each of which will lead to a point on the Pareto front. In this example, there are five input dose distributions, and five corresponding points A, B, C, D, E on the Pareto front. For point A, the second objective function $f_2$ has a high value but the first objective function $f_1$ has a low value, which is more desirable. For point E, the first constituent function $f_1$ has a high, poorer value but the second constituent function $f_2$ has a low, better value, compared to point A. For the intermediary points B, C, D the values of both objective functions are between the ones for the outermost points A and E. FIG. 2 also shows a point x which is interpolated between points D and E, by a weighted sum of the dose distributions generating these two points.

At the essence of multi-criteria optimization is finding the point on the closed curve or inside the shaded region, in other words, the weighted sum of all the input dose distributions, that will result in best possible clinical outcome for the patient. As the exact outcome is unknown at the timepoint when the navigated dose distribution is selected, the selection of the most preferred plan is an in-part subjective choice on the behalf of the clinicians. This may be a point on the Pareto front, or a point within the volume defined by all feasible solutions, the latter being indicated by a point y inside the volume.

According to the invention, after the interpolated plan has been obtained, as outlined above, an automatic navigation is performed for further optimization of the dose. In this automatic navigation, a new optimization problem is defined based on clinical goals provided by the clinicians.

Because there is a linear relationship between the dose distribution of each input plan and the total dose distribution in the navigated plan, and the clinical goals, the effect of changing the contribution of one plan to the navigated plan can be predicted for the whole treatment volume.

In the simplest case, there is one set of clinical goals that all have the same priority. In a more complex case, the set of clinical goals may be divided into subsets, one subset having the highest priority and one or more further subsets in falling priority order to take into account that some clinical goals may be more important than others.

Figure 3:
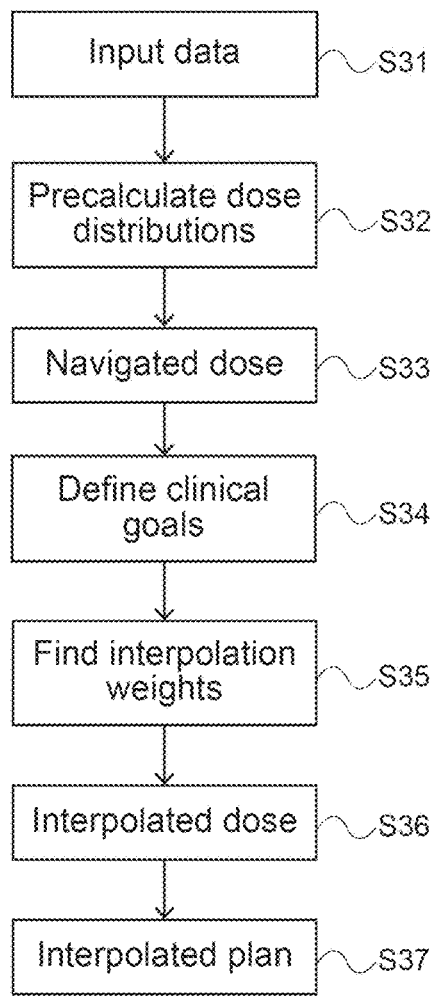
FIG. 3 is a flow chart of a method according to the invention.

FIG. 3 is a flow chart of the method according to the invention. In a first step S31, input data to the method are determined. Step 31 may be performed at any time prior to the following steps. The input data comprise a multi-criteria optimization problem comprising a set of objective functions related. In step S32, a set of treatment plans are calculated based on the optimization problem and the resulting dose distribution for each input plan is determined. These dose distributions will be referred to as the input dose distributions, to be weighted together into a navigated dose distribution. It is possible, although less advantageous, to use a number of dose distributions calculated from a number of input plans that are not related to each other in any particular way as input dose distributions. In recent years, it is also possible to determine a desired dose distribution for a particular patient geometry without first calculating a treatment plan. In other words, the input dose distributions do not have to be based on plans resulting from the same multi-criteria optimization problem, although this is the preferred embodiment. The input dose distributions do not have to be based on a treatment plan at all. The important thing is that a set of input dose distributions is provided.

In step S33 a navigated dose distribution is obtained based on the input dose distributions. This may involve defining a parameter weight for each input dose distribution and applying the parameter weight to create the navigated dose distribution. This navigated dose distribution may be the starting point for automatic optimization according to the invention. Alternatively, the automatic dose distribution may start directly from the input dose distributions without first obtaining a navigated dose distribution. In other words, step S33 is an optional step.

In the following steps, the input dose distributions may be input dose distributions obtained by the steps S31-S32, or in any other suitable way, and a navigated dose distribution obtained in step S33 may be used as start values for the interpolation weights. The subsequent optimization may be started automatically when the input data are available, or may be started manually by user input. The optimization may be stopped by user input if such input means are provided in the user interface. Alternatively, the optimization may be stopped automatically when the clinical goals are fulfilled. In step S34, a set of clinical goals for a particular patient are determined. The clinical goals may be related or unrelated to the objective functions. A prioritized list of clinical goals may be defined, so that fulfilling clinical goals with a higher priority is considered more important than fulfilling clinical goals with a lower priority. Of course, step S34 may be performed at any time prior to step S35, in which the clinical goals are used.

In step S35 a set of interpolation weights for the input dose distributions is determined. The interpolation weights are expressed in terms of a weight vector comprising an interpolation weight for each dose distribution, each interpolation weight determining the contribution this input dose distribution should make to the interpolated dose, relative to the other input dose distributions. In step S36, the resulting interpolated dose distribution may be obtained as a weighted sum of the input dose distributions, by applying the interpolation weights to the input dose distributions. The resulting weighted sum should fulfil the clinical goals to the greatest possible extent. According to the invention, the interpolation weights are based directly on adjusting the contribution made by each of the input dose distributions to the interpolated dose distribution. In other words, the dose distributions are weighted such that the weighted sum of all the input dose distributions results in the desired dose distribution.

In step S36 the resulting interpolated dose distribution is converted to a treatment plan. If the input dose distribution has been based on dose distributions obtained from input treatment plans, this involves applying the interpolation weights to interpolation of the variables of the input plans (the variables x in the multi-criteria optimization problem). Such interpolation is possible for treatment delivery techniques where the relationship between variables and dose is linear, or approximately linear, e.g., if the variables represent ion beam spot weights or fluence maps for external beam photon treatments. If the input dose distribution has been obtained without any treatment plan, an interpolated treatment plan may be obtained by solving an optimization problem defined to minimize the deviation between the interpolated dose distribution and the dose distribution for the optimized plan.

The interpolated dose distribution or interpolated variables may also be used as a starting point for further optimization of the dose distribution before converting to a treatment plan. For example, an optimization that minimizes the error between a dose distribution associated with a feasible treatment plan and the interpolated dose distribution may be performed for delivery techniques where the relationship between variables and dose distributions is non-linear.

The method may be expanded by repeating step S33 and/or steps S35 and S36 whenever this is desired. It is possible to move between the manual navigation of step S33 and the interpolation in S36-S37, respectively, as many times as desired. Between the iterations, one or more clamps or constraints on clinical goals may be added to ensure that a desired output from one iteration is not discarded in a later iteration.

The search in step S35 for interpolation weights that best meet the specified clinical goals may be implemented as an optimization where the interpolation weights y constitute the decision variables. The user requirements may be reflected by an optimization function $f$ to be minimized and, optionally, a vector g of constraint functions that are feasible when non-positive and a vector h of constraint functions that are feasible when zero.

Mathematically, the method, in the case of all clinical goals having the same priority, may be expressed as the following optimization problem:

$$\text{minimize } f(y)$$
$$\text{subject to } y \geq 0,$$
$$g(y) \leq 0,$$
$$h(y) = 0,$$

where y is the vector of interpolation weights and g and h are vectors of constraint functions. In one preferred embodiment, the vector of equality-constrained functions h includes the function $e^T y - 1$, where e is the vector of all ones, which ensures that the interpolation weights sum to one. The objective function $f$ in this automatic navigation is a measure of how much the navigated dose distribution deviates from the clinical goals. This is expressed in terms of a vector of weights $y_j$, each weight determining the contribution of one of the input plans to the navigated dose distribution.

If the set of clinical goals is divided into a number k of subsets assigned different priority levels, this can be expressed mathematically as:

$$\text{lex minimize } f_1(y), \ldots, f_k(y)$$
$$\text{subject to } y \geq 0,$$
$$g(y) \leq 0$$
$$h(y) = 0,$$

where "lex minimize" indicates that the optimal y is the solution that minimizes the optimization functions $f_1$ to $f_k$, in the specified order. In other words, the optimization will be performed for one optimization function at a time, in the specified order. After each optimization of an optimization function, constraints are added to avoid that a lower priority optimization function would lead to a deterioration in the fulfilment of an optimization function having a higher priority.

If the goal of automated interpolation is to fulfil user-specified clinical goals, then the optimization function may be a sum of constituent functions that each measure the violation of one of the goals. The components of the vector of constraints may reflect already satisfied clinical goals that should be kept in a fulfilled state. The automated optimization problem is in general a continuous non-linear optimization problem that may be solved using standard non-linear programming methods, such as an interior point method or a sequential quadratic programming method.

Figure 4:
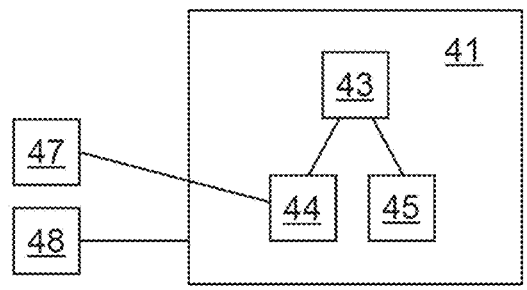
FIG. 4 discloses a computer system in which the method according to the invention may be implemented.

FIG. 4 is a schematic drawing of a computer system in which the method according to the invention may be performed. A computer 41 comprises a processor 43, a data memory 44 and a program memory 46. Preferably, one or more user input means 48 are also present, in the form of a keyboard, a mouse, a joystick, voice recognition means or any other available user input means. Also, a display 49 is preferably present, comprising a screen for displaying the interface discussed in connection with FIG. 1b. The user input means 48 may also be used to input data into the interface. The user input means may also be arranged to receive data from an external memory unit.

The data memory 34 comprises data to be used in the procedure, such as the input plans and clinical goals. The program memory 36 holds a computer program arranged to make the computer perform the method steps discussed in connection with FIG. 3.

As will be understood, the data memory 34 and the program memory 36 are shown and discussed schematically.

There may be several data memory units, each holding one or more different types of data, or one data memory holding all data in a suitably structured way, and the same holds for the program memories. For example, there may be separate memories or memory segments for precalculated plans, clinical goals and navigated dose distributions, respectively. One or more memories may also be stored on other computers.

The invention claimed is:

1. A method of optimization of a radiation treatment plan for a patient, comprising the following steps:
   providing a set of input dose distributions;
   defining an interpolation optimization problem based on a set of clinical goals for the patient, the interpolation optimization problem comprising a set of optimization functions, at least one optimization function representing a measure of violation of a clinical goal in the set of clinical goals;
   optimizing an interpolated dose distribution based on a weighted combination of the input dose distributions, by a computer-based optimization of the interpolation optimization problem, said optimization involving determining, for each of the input dose distributions, an interpolation weight, specifying the weight to be assigned to this input dose distribution in a further optimized dose distribution; and
   calculating an interpolated treatment plan based on the interpolated dose distribution.

2. The method according to claim 1, wherein the step of providing the set of input dose distributions comprises obtaining a set of input plans and calculating an input dose distribution for each of the input plans.

3. The method according to claim 1, wherein the step of providing the set of input dose distributions comprises
   a. providing a multi-criteria optimization problem including a set of at least two objective functions;
   b. obtaining a set of input treatment plans by optimization with respect to the multi-criteria optimization problem; and
   c. calculating a set of precalculated dose distributions, each dose distribution being associated with one of the treatment plans.

4. The method according to claim 1, further comprising the step, before the optimization of the interpolated dose distribution, of providing a navigated dose distribution based on a weighted combination of the input dose distribution, in which each input dose distribution is assigned a navigation weight, and using the navigation weights as input values to the optimization.

5. The method according to claim 1, further comprising manual navigation of the interpolated dose distribution before calculating the interpolated treatment plan.

6. The method according to claim 1, wherein the step of optimizing the interpolated dose distribution is performed in dependence of at least one constraint.

7. The method according to claim 1, wherein the interpolation optimization problem is expressed as $$\text{minimize } f(y)$$

subject to $y \geq 0$, and including at least one constraint vector $$g(y) \leq 0, \text{ and/or } h(y) = 0,$$

where y is the vector of interpolation weights.

8. The method according to claim 1, wherein the step of providing the set of clinical goals involves providing a first and a second subset of clinical goals, the second subset comprising clinical goals that have a lower priority than the first subset, and the step of optimizing the set of interpolation weights involves first optimizing interpolation weights for the first subset of clinical goals, and in a subsequent operation refining the interpolation weights based on the second subset of clinical goals, the subsequent operation being subject to constraints based on the interpolation weights optimized for the first subset.

9. The method according to claim 6, where at least one constraint corresponds to a limit restricting an objective function value of the interpolated treatment plan, the limit corresponding to a clamp on a slider bar.

10. A user interface for controlling optimization of a radiation treatment plan carried out in a computer, based on a number of input treatment plans, according to claim 1, comprising:
   a display for displaying a list of clinical goals and an associated value range for each clinical goal, and an indicator of whether the clinical goal is fulfilled; and
   an input enabling a user to start optimization according to claim 1.

11. The user interface according to claim 10, wherein the list of clinical goals is also arranged to hold an associated constraint for at least one of the clinical goals, and an indicator of whether the constraint is fulfilled.

12. The user interface according to claim 10, wherein the input is configured to enable a user to enter clinical goals and/or other input data affecting the optimization problem into the computer.

13. A computer program product for controlling a radiation therapy planning apparatus, stored on a non-transitory storage means, said computer program product comprising computer readable code means which when run in a processor of a radiation therapy planning apparatus will cause the apparatus to perform the method according to claim 1.

14. The computer program product according to claim 13, wherein the computer readable code means, when run in the processor of the radiation therapy planning apparatus, will cause a user interface to be displayed, the user interface for controlling optimization of the radiation treatment plan carried out in the computer, based on a number of input treatment plans, the user interface comprising:
   a display for displaying a list of clinical goals and an associated value range for each clinical goal, and an indicator of whether the clinical goal is fulfilled; and
   an input enabling a user to start optimization,
   wherien the user interface is configured to be displayed on a screen associated with the radiation therapy planning apparatus, register an adjustment to an interpolation weight to be assigned to a treatment plan and calculate the further optimized treatment plan as a weighted sum of the input treatment plans, using each interpolation weight as a weight for its associated input treatment plan.

15. A radiation therapy treatment planning apparatus comprising a processor and a program memory holding a computer program product according to claim 13, arranged to be run in the processor to control the radiation therapy treatment planning apparatus.

* * * * *